(12) United States Patent
Tanaka et al.

(10) Patent No.: US 8,920,784 B2
(45) Date of Patent: Dec. 30, 2014

(54) ANTIBACTERIAL ARTIFICIAL NAIL COMPOSITION

(75) Inventors: Hisaki Tanaka, Kyoto (JP); Mikito Deguchi, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 215 days.

(21) Appl. No.: 13/207,818

(22) Filed: Aug. 11, 2011

(65) Prior Publication Data

US 2011/0293546 A1 Dec. 1, 2011

Related U.S. Application Data

(62) Division of application No. 12/585,828, filed on Sep. 25, 2009, now abandoned.

(30) Foreign Application Priority Data

Sep. 25, 2008 (JP) .................................. 2008-245927

(51) Int. Cl.
*A61K 8/02* (2006.01)
*A61L 33/02* (2006.01)
*A61Q 3/02* (2006.01)
*A61K 8/24* (2006.01)
*A61K 8/26* (2006.01)
*A61K 8/81* (2006.01)
*A61Q 17/00* (2006.01)

(52) U.S. Cl.
CPC ..... *A61Q 3/02* (2013.01); *A61K 8/24* (2013.01); *A61K 8/26* (2013.01); *A61K 8/8152* (2013.01); *A61Q 17/005* (2013.01)
USPC .............................................. 424/61; 427/2.1

(58) Field of Classification Search
None
See application file for complete search history.

(56) References Cited

U.S. PATENT DOCUMENTS

| 4,911,898 | A | * | 3/1990 | Hagiwara et al. ............. 423/700 |
| 5,468,489 | A | * | 11/1995 | Sakuma et al. ................. 424/49 |
| 2001/0056133 | A1 | * | 12/2001 | Montgomery et al. ........ 523/113 |
| 2004/0229973 | A1 | * | 11/2004 | Sang et al. ..................... 523/118 |
| 2005/0245671 | A1 | | 11/2005 | Moon et al. |
| 2007/0197372 | A1 | | 8/2007 | Kurihara et al. |
| 2007/0286827 | A1 | | 12/2007 | Sheariss et al. |

FOREIGN PATENT DOCUMENTS

| JP | 8-165216 | | 6/1996 | |
| JP | 2004-189661 | | 7/2004 | |
| JP | 2004189661 | * | 7/2004 | ............. A61K 6/083 |
| JP | 2005-530547 | | 10/2005 | |
| JP | 2007-223925 | | 9/2007 | |

* cited by examiner

*Primary Examiner* — Kortney L Klinkel
*Assistant Examiner* — Melissa Javier
(74) *Attorney, Agent, or Firm* — Wenderoth, Lind & Ponack, L.L.P.

(57) ABSTRACT

The present invention provides an antibacterial artificial nail composition which can form a cured article having an antibacterial effect by applying the composition on a surface of a natural nail or an artificial nail and polymerizing the composition, using an artificial nail technique of forming a cured article on a natural nail or an artificial nail.

Disclosed is an antibacterial artificial nail composition comprising (A) a compound having at least one radical polymerizable unsaturated double bond and an antibacterial group in the molecule and/or (B) an antibacterial filler, (C) a compound having at least one radical polymerizable unsaturated double bond in the molecule, and (D) a polymerization initiator.

13 Claims, No Drawings

ANTIBACTERIAL ARTIFICIAL NAIL COMPOSITION

This application is a divisional of U.S. application Ser. No. 12/585,828, filed Sep. 25, 2009, now abandoned.

BACKGROUND OF THE INVENTION

1. Field of the Invention

The present invention relates to an artificial nail composition to be formed on a natural nail or an artificial nail, which is used by applying the composition on a surface of the natural nail or the artificial nail and polymerizing the composition. More particularly, the present invention relates to an antibacterial artificial nail composition containing a (meth)acrylic acid ester compound having a 10-undecenoxy group and an ethoxy group, an antibacterial filler, a polymerizable monomer and a polymerization initiator. Use of the composition of the present invention provides an artificial nail composition whose cured article has the antibacterial effect.

2. Description of the Related Art

Nail art means makeup or decoration of nails of the hands and feet. A shop for nail art is called a nail salon and a nail art technician is called a nailist. Various nail art goods are commercially available and there are many women who perform nail art with skill equivalent to a professional.

An artificial nail material in which a dental normal temperature polymerization resin is applied is excellent in strength and durability when compared with a manicure in which a lacquer coating material is applied, and is therefore accepted by some professional nailists. However, because of stimulation derived from an acrylic monomer, irritating odor and poor operability, the artificial nail material did not sufficiently spread among general nailists.

Recently, a gel nail having improved odor stimulation or operability of the artificial nail material using the dental normal temperature polymerization resin has dominated the market. A gel nail which is currently commercially available is a high-viscosity liquid material containing a (meth)acrylic monomer and a photopolymerization initiator as main constituent components, and is cured by irradiation with ultraviolet rays. The commercially available gel nail is less likely to cause odor stimulation and skin stimulation and has satisfactory operability, and is also rich in color when compared with the aforementioned artificial nail material in which a dental normal temperature polymerization resin is applied. Therefore, the commercially available gel nail is now accepted by a lot of general nailists.

Furthermore, the gel nail is characterized in that it exhibits satisfactory durability of an artificial nail and can maintain beautiful appearance for several weeks when compared with a conventional manicure in which a lacquer coating material is applied and a conventional artificial nail material in which a dental normal temperature polymerization resin is applied. However, there is a problem that various nail disorders and diseases onset under an insanitary environment in a state where an artificial nail is attached over a long period. One example of nail disorders and diseases is generally so-called green nail caused by propagation of a kind of molds on the nail, which is *Pseudomonas aeruginosa* infection and is caused by secondary bacterial infection, and perionychia, nail tinea and onycholysis are also exemplified. Such infection is a familiar example and an artificial nail composition having antibacterial properties is desired.

Undecylenic acid or a derivative thereof, for example, an ester and a metal salt thereof, particularly an alkali metal salt or an alkali earth metal salt is known for its various characteristics. For example, pediculicidal activity of undecylenic acid or a derivative thereof, particularly a lower alkyl ester derivative is reported in Japanese Patent No. 3,127,289, and JP-A No. 10-53522. Also, antibacterial activity of undecylenic acid is reported in JP-A No. 10-158162.

JP-A No. 2004-210665 discloses an antibacterial treating agent containing, as an active ingredient, an esterified compound prepared by an esterification reaction of undecylenic acid and a compound having a polymerizable unsaturated group. Specifically, the antibacterial treating agent has a feature that antibacterial activity lasts over a long period since it has a wide antibacterial spectrum ranging from true fungi to Eumycota and has remarkably high antibacterial activity and is also immobilized in a polymer when the antibacterial treating agent of the present invention is processed into fibers. Also, since the antibacterial treating agent can be used using a very small amount of a resin and has no toxicity, it can be widely applied and exerts a remarkable effect capable of exerting the antibacterial effect over a long period.

Regarding an antibacterial filler, JP-A No 8-165216 discloses that a Ag, Cu, Zn, Ni-substituted type filler represented by the general formula 2 exhibits satisfactory antibacterial properties against molds.

JP-A No. 8-245326 discloses a method for producing a zeolite, and Japanese Patent Publication No. 2,512,324 discloses that a Ag, Cu, Zn-substituted type zeolite is effective against halitosis or stomatitis.

SUMMARY OF THE INVENTION

An object of the present invention is to provide an antibacterial artificial nail composition which can form a cured article having the antibacterial effect by applying the composition on a surface of a natural nail or an artificial nail and polymerizing the composition, using an artificial nail technique of forming a cured article on a natural nail or an artificial nail.

The present invention provides an antibacterial artificial nail composition containing a (meth)acrylic acid ester compound having a 10-undecenoxy group and an ethoxy group represented by the following general formula 1 (compound A) and/or an antibacterial filler represented by the general formula 2 or 3:

[Chemical Formula 1]

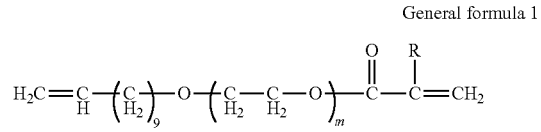

General formula 1 wherein m represents an integer of 0 to 18, and R represents a hydrogen atom or a methyl group.

$$Ca_{10-x}M_{2x/n}(PO_4)_6(OH)_2 \quad \text{General formula 2}$$

$$XM1_{2/n}O \cdot Al_2O_3 \cdot YSiO_2 \cdot ZH_2O \quad \text{General formula 3}$$

The present invention also provides an antibacterial artificial nail composition which contains the (meth)acrylic acid ester compound (A) in an amount of 0.1 to 70% by weight based on the entire amount of the composition, a cation-substituted type hydroxyapatite-based antibacterial filler represented by the general formula 2 in an amount of 0.5 to 7.5% by weight based on the entire amount of the composition, or a zeolite-based antibacterial-filler represented by the general formula 3 in an amount of 0.5 to 7.5% by weight based on the entire amount of the composition.

The present invention also provides the antibacterial artificial nail composition, which further contains another polymerizable monomer (C).

According to the antibacterial artificial nail composition of the present invention, an artificial nail material capable of permanently lasting antibacterial activity is provided.

DETAILED DESCRIPTION OF THE INVENTION

In the present invention, the (meth)acrylic acid ester compound (A) having a 10-undecenoxy group and an ethoxy group described in the formula I can be prepared, for example, by a reaction of undecenol, (meth)acrylic acid and ethylene oxide.

Since undecenol is obtained by reducing undecylenic acid obtained from thermolysis of a castor oil, the compound (A) described in the formula I imposes a small burden on the global environment, and since it is composed of carbon, oxygen and hydrogen, it has high safety, and also has excellent performances as a dental antibacterial agent. Since the effect against filamentous fungi such as *Trichophyton* has been recognized for a long time, undecylenic acid as an oxide of undecenol is registered as a drug and is also used as a cosmetic material (antiseptic sterilizer).

In the formula I, m represents an integer of 0 to 18, R represents a hydrogen atom or a methyl group, and m is preferably from 6 to 15.

This compound (A) represented by the formula I has a 10-undecenoxy group as an antibacterial site in the structure and, regarding a cured article of a dental polymerizable composition containing the same, the antibacterial site is immobilized and is not eluted, and thus it is expected to have permanent antibacterial activity.

The antibacterial artificial nail composition of the present invention can contain the (meth)acrylic acid ester compound (A) in an amount of 0.1 to 70% by weight, and preferably 1 to 60% by weight, based on the entire amount of the artificial nail composition by the following reason. When the amount is less than 0.1% by weight, the obtained composition has not sufficient antibacterial activity. In contrast, when the amount exceeds 60% by weight, adverse influence may be exerted on the mechanical strength as the antibacterial artificial nail composition.

Another polymerizable monomer (C) used in the present invention is used as a polymerizable component of the antibacterial artificial nail composition and is preferably copolymerizable with the (meth)acrylic acid ester compound (A), and examples thereof include, but are not limited to, a radical polymerizable monomer.

Examples of the radical polymerizable monomer include conjugated diene monomers such as butadiene, and isoprene; aromatic vinyl monomers such as styrene, a-methylstyrene, and chlorostyrene; vinyl cyanide monomers such as acrylonitrile, and methacrylonitrile; vinyl halides and vinylidenes, such as vinyl chloride, vinyl bromide, vinylidene chloride, and vinylidene bromide; vinyl esters such as vinyl acetate, and vinyl propionate; (meth)acrylic acid (hereinafter referred to as a generic term of acrylic acid and methacrylic acid) esters listed below; polymerizable monomers having at least one carboxyl group in one molecule; and polymerizable monomers having at least one phosphoric acid group or sulfone group in one molecule. These monomers are used alone for polymerization, together with the (meth)acrylic acid ester compound (A), or two or more kinds of monomers are used in combination.

As the (meth)acrylic acid esters which can be used as the polymerizable monomer (C), for example, linear alkyl (meth)acrylates, and branched alkyl (meth)acrylates having C1-C4 alkyl, such as methyl (meth)acrylate, ethyl (meth)acrylate, an n- or i-propyl ester of (meth)acrylic acid, and an n-, i- or t-butyl ester (meth)acrylic acid are preferably used. The (meth)acrylic acid esters further include aliphatic esters such as 2-ethylhexyl(meth)acrylate, benzyl (meth)acrylate, methoxyethyl (meth)acrylate, glycidyl (meth)acrylate, methylol (meth)acrylamide, N,N-dimethylaminoethyl (meth)acrylate, N,N-diethylaminoethyl (meth)acrylate, 2-hydroxyethyl (meth)acrylate, 2- or 3-hydroxypropyl (meth)acrylate, 2- or 3-methoxypropyl (meth)acrylate, glycerol mono(meth)acrylate, diethylene glycol mono(meth)acrylate, methoxydiethylene glycol mono(meth)acrylate, triethylene glycol mono (meth)acrylate, methoxytriethylene glycol mono(meth)acrylate, pentaethylene glycol mono(meth)acrylate, methoxypentaethylene glycol mono(meth)acrylate, polyethylene glycol mono(meth)acrylate, methoxypolyethylene glycol mono(meth)acrylate, 2-hydroxy-3-phenoxypropyl (meth)acrylate tetrahydrofurfuryl (meth)acrylate, neopentylglycol di(meth)acrylate, and trimethylolpropane tri(meth)acrylate; monofunctional (meth)acrylates or (meth)acrylic acid amides, such as 2-hydroxyethyl (meth)acrylate, 2- or 3-hydroxypropyl (meth)acrylate, glycerol mono(meth)acrylate, diethylene glycol mono(meth)acrylate, triethylene glycol mono(meth)acrylate, pentaethylene glycol mono(meth)acrylate, polyethylene glycol mono(meth)acrylate, 2-hydroxy-3-phenoxypropyl (meth)acrylate, methylol (meth)acrylamide, and hydroxyl group-containing (meth)acrylates such as an adduct of 1 mol of bisphenol A and 2 mol of glycidyl (meth)acrylate; polyethylene glycol di(meth)acrylates such as ethylene glycol di(meth)acrylate, diethylene glycol di(meth)acrylate, triethylene glycol di(meth)acrylate, pentaethylene glycol di(meth)acrylate, nonaethylene glycol di(meth)acrylate, and tetradecaethylene glycol di(meth)acrylate; polypropylene glycol di(meth)acrylates such as propylene glycol di(meth)acrylate, dipropylene glycol di(meth)acrylate, tripropylene glycol di(meth)acrylate, and nonapropylene glycol di(meth)acrylate; mono(meth)acrylates in which (meth)acryloyl groups of either the polyethylene glycol di(meth)acrylate or polypropylene glycol di(meth)acrylates are substituted with methyl groups and ethyl groups; (meth)acrylates having a urethane bond, such as butylene glycol di(meth)acrylate, propanediol di(meth)acrylate, hexanediol di(meth)acrylate, 2-(meth)acryloyloxyethyl isocyanate, and an adduct of 2,2,4-trimethylhexamethylene diisocyanate or 1,3,5-trimethylhexamethylene diisocyanate and 2-hydroxyethyl(meth)acrylate; and 2,2-bis(4-(meth)acryloyloxypolyethoxyphenyl)propanes obtained by condensing a product, which is obtained by adding oxyethylene to bisphenol A, with (meth)acrylic acid.

Examples of the polymerizable monomer having at least one carboxyl group in one molecule include monocarboxylic acid, dicarboxylic acid, tricarboxylic acid and tetracarboxylic acid or derivatives thereof. Specific examples thereof include (meth)acrylic acid, maleic acid, p-vinylbenzoic acid, 11-(meth)acryloyloxy-1,1-undecanedicarboxylic acid (MAC-10), 1,4-di(meth)acryloyloxyethylpyromellitic acid, 6-(meth)acryloyloxyethylnaphthalene-1,2,6-tricarboxylic acid, 4-(meth)acryloyloxymethyltrimellitic acid and an anhydride thereof, 4-(meth)acryloyloxyethyltrimellitic acid and an anhydride thereof, 4-(meth)acryloyloxybutyltrimellitic acid and an anhydride thereof, 4-[2-hydroxy-3-(meth)acryloyloxy]butyltrimellitic acid and an anhydride thereof, 2,3-bis(3,4-dicarboxybenzoyloxypropyl (meth)acrylate, N,O-di(meth)acryloyloxytylosin, O-(meth)acryloyloxytylosin, N-(meth)acryloyloxytylosin, N-(meth)acryloyloxyphenylalanine, N-(meth)acryloyl p-aminobenzoic acid, N-(meth)acryloyl-O-aminobenzoic acid, N-(meth)acryloyl 5-aminosalicylic acid, N-(meth)acryloyl 4-aminosalicylic acid, 2- or 3- or 4-(meth)acryloyloxybenzoic acid, an addition product of 2-hydroxyethyl(meth)acrylate and pyromellitic dianhydride (PMDM), an addition reaction product of 2-hydroxyethyl (meth)acrylate and maleic anhydride or 3,3',4,4'-benzophenonetetracarboxylic dianhydride (BTDA) or 3,3',4,4'-biphenyltetracarboxylic dianhydride, an adduct of 2-(3,4-dicarboxybenzoyloxy) 1,3-di(meth)acryloyloxypropane, N-phenylglycine or N-tolylglycine and glycidyl (meth)acrylate, 4-[(2-hydroxy-3-(meth)acryloyloxypropyl)amino]phthalic acid, and 3- or 4-[N-methyl N-(2-hydroxy-3-(meth)acryloyloxypropyl)amino]phthalic acid.

Examples of the polymerizable monomer having at least one phosphoric acid group or sulfone group in one molecule include 2-(meth)acryloyloxyethyl acid phosphate, 2- and 3-(meth)acryloyloxypropyl acid phosphate, 4-(meth)acryloyloxybutyl acid phosphate, 6-(meth)acryloyloxyhexyl acid phosphate, 8-(meth)acryloyloxyoctyl acid phosphate, 10-(meth)acryloyloxydecyl acid phosphate, 12-(meth)acryloyloxydodecyl acid phosphate, bis{2-(meth)acryloyloxyethyl} acid phosphate, bis{2 or 3-(meth)acryloyloxypropyl} acid phosphate, 2-(meth)acryloyloxyethylphenyl acid phosphate, and 2-(meth)acryloyloxyethyl p-methoxyphenyl acid phosphate. Phosphoric acid groups in these compounds can be substituted with thiophosphoric acid groups. Among these, 2-(meth)acryloyloxyethylphenyl acid phosphate, 10-(meth)acryloyloxydecyl acid phosphate, 2-sulfoethyl (meth)acrylate, 2 or 1-sulfo-1 or 2-propyl(meth)acrylate, 1 or 3-sulfo-2-butyl (meth)acrylate, 3-bromo-2-sulfo-2-propyl(meth)acrylate, 3-methoxy-1-sulfo-2-propyl(meth)acrylate, and 1,1-dimethyl-2-sulfoethyl (meth)acrylamide can be exemplified.

The antibacterial artificial nail composition of the present invention can contain the polymerizable monomer (B) in an amount of 1 to 99.9% by weight based on the entire amount of the composition.

In the present invention, a polymerization initiator can be used so as to obtain the antibacterial artificial nail composition. The polymerization initiator also includes a curing agent and an accelerator. The composition preferably contains at least one kind described below and the polymerization initiator can be used in combination in conformity with use conditions.

The polymerization initiator includes a polymerization initiator which can perform radical polymerization of a polymerizable monomer, and examples thereof include organic peroxides such as diacetyl peroxide, dipropyl peroxide, dibutyl peroxide, dilauryl peroxide, benzoyl peroxide (BPO), p,p'-dichlorobenzoyl peroxide, p,p'-dimethoxybenzoyl peroxide, p,p'-dimethylbenzoyl peroxide, and p,p'-dinitrodibenzoyl peroxide; and organic boron compounds such as a partial oxide of trialkylborane or trialkylborane.

It is also possible to polymerize by irradiating with ultraviolet rays or visible rays. As the antibacterial artificial nail composition of the present invention, a known photopolymerization initiator can be used. Examples of the photopolymerization initiator are benzoinethers, benzylketals, a-dialkoxyacetophenones, a-hydroxyalkylphenones, a-aminoalkylphenone, acylphosphine oxides, benzophenones, and thioxanthones, titanocenes, and preferably 2-hydroxy-2-methylpropiophenone and acylphosphine oxides.

The composition usually contains the polymerization initiator (D) in an amount of 0.01 to 10 parts by weight based on 100 parts by weight of the entire polymerizable monomer (for example, the (meth)acrylic acid ester compound (A) alone, or the total of the ester compound (A) and another polymerizable monomer (C)).

When an organic peroxide or a photopolymerization initiator is used as the polymerization initiator (D), a reducing compound can be used in combination.

It is possible to use, as the organic reducing compound, aromatic amines such as N,N-dimethylaniline, N,N-dimethyl-p-toluidine (DMPT), N,N-diethyl-p-toluidine, N,N-diethanol-p-toluidine (DEPT), N,N-dimethyl p-tert-butylaniline, N,N-dimethylanisidine, N,N-dimethyl-p-chloroaniline, N,N-dimethylaminoethyl (meth)acrylate, N,N-diethylaminoethyl (meth)acrylate, N,N-dimethylaminobenzoic acid and an alkyl ester thereof, N,N-diethylaminobenzoic acid (DEABA) and an alkyl ester thereof, and N,N-dimethylaminobenzaldehyde (DMABAd); and amines such as N-phenylglycine (NPG), N-tolylglycine (NTG), and N,N-(3-methacryloyloxy-2-hydroxypropyl)phenylglycine (NPG-GMA) in combination. Among these amines, DMPT, DEPT, DEABA, DMABAd, NPG and NTG can be preferably used. It is also possible to use aromatic sulfinic acids such as benzenesulfinic acid, o-toluenesulfinic acid, p-toluenesulfinic acid, ethylbenzenesulfinic acid, decylbenzenesulfinic acid, dodecylbenzenesulfinic acid, chlorobenzenesulfinic acid, naphthalenesulfinic acid, or salts thereof; thiol esters of aromatic sulfinic acids; and aromatic sulfinic acid amides in combination.

In order to obtain an artificial nail composition in the present invention, the composition can contain a filler, if necessary. Examples of the filler include an organic filler, an inorganic filler, or an organic composite filler containing both of the organic filler and the inorganic filler, which have hitherto been used. Examples of a soluble high molecular weight polymer which has hitherto been used include homopolymers or polymers of methyl (meth)acrylate, ethyl (meth)acrylate, propyl(meth)acrylate and butyl(meth)acrylate; polymers obtained by copolymerizing these homopolymers or polymers with 5% or less of ethylene glycol di(meth)acrylate as a crosslinking agent; vinyl polyacetate, polyethylene glycol (PEG), polypropylene glycol (PPG), and polyvinyl alcohol (PVA).

Examples of the inorganic filler include amorphous silica, alumina, quartz, alumina quartz, a silica-alumina compound, a silica-zirconia compound, a silica-titania compound, titanium oxide, glass (including barium glass), zirconium hydroxide, calcium carbonate, kaolin, clay; mica, aluminum sulfate, barium sulfate, calcium sulfate, calcium phosphate, and hydroxyapatite. These inorganic fillers may be preliminarily surface-treated with a silane coupling agent or a titanate coupling agent.

Examples of the organic composite filler include fillers obtained by coating a surface of the inorganic filler with a polymerizable monomer through polymerization, and grinding the coated inorganic filler. Specific examples thereof include fillers (TMPT·f) obtained by coating fine powdered silica among inorganic fillers with a polymerizable monomer containing trimethylolpropane tri(meth)acrylate (TMPT) as a main component through polymerization and grinding the obtained coated polymer, and tillers obtained by adding an such as silica and zirconium hydroxide in a solution of acetone containing PMMA dissolved therein thereby dispersing the inorganic filler, and distilling off the solvent, followed by drying and further grinding.

An average particle size of these fillers is preferably within a range from 0.1 to 100 μm, and it is more preferred to use fillers, each having a different particle diameter; after mixing. The content of the filler varies depending on the applications and is usually from 10 to 600 parts by weight based on 100 parts by weight (total amount) of the compound (A) and another polymerizable monomer (C).

Furthermore, the antibacterial dental polymerizable composition of the present invention can contain water and/or a water-soluble organic solvent such as acetone, ethanol or the like in an amount of 5 to 95% by weight.

The artificial nail composition of the present invention can be mixed with known various additives, if necessary. Examples of the additive include oily materials such as oils and fats, waxes, hydrocarbon, higher fatty acid, higher alcohols and esters; moisturizing/wetting agents; extracted essence of plants; drugs such as skin lightening agent, vitamin agent, hormone agent, antipruritic agent/anti-itch agent, anti-inflammatory agent/antiphlogistic agent, keratolytic agent/keratin peeling agent, astringent, antioxidant, antibacterial agent/antiseptic sterilizer and ultraviolet absorbing agent; surfactants; coloring agents/color pigments; perfumes; thickeners; film-coating agents; polymerization inhibitors; antitarnish agents; fluorescent agents; and volatile organic solvents.

EXAMPLES

The present invention will be specifically explained by way of Examples, but the present invention is not limited to the following Examples.

Abbreviations of Compounds Used in Examples of the Present Invention 1. (Meth)Acrylic Acid Ester Compound (A) Having a 10-Undecenoxy Group and an Ethoxy Group ML-12G: (meth)acrylic acid ester compound having a 10-undecenoxy group and an ethoxy group represented by the following formula I

[Chemical Formula 2]

formula I

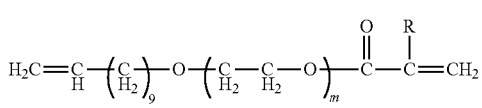

(m=12)

ML-8G: (meth)acrylic acid ester compound having a 10-undecenoxy group and an ethoxy group represented by the following formula I

[Chemical Formula 3]

formula I

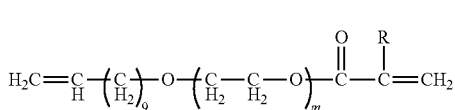

(m=8)

ML: (meth)acrylic acid ester compound having a 10-undecenoxy group and an ethoxy group represented by the following formula I

[Chemical Formula 4]

formula I

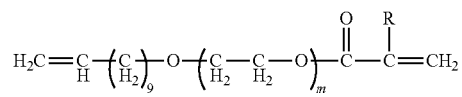

(m=0)

2. Antibacterial Filler (B)

Cation-substituted type hydroxyapatite-based antibacterial filler (antibacterial filler A):

Zeolite-based antibacterial filler (antibacterial filler B):

3. Another Polymerizable Monomer (C)

UDMA: dimethacryloxyethyl-2,2,4-rimethylhexamethylenediurethane

BisMEP: bis[2-(methacryloxy)ethyl]phosphate

UDAO: urethaneacrylate oligomer (molecular weight: 15,000, number of functional groups: 2)

2HEMA: 2-hydroxyethyl methacrylate

4. Polymerization Initiator (D)

MAPO: 2,4,6-trimethylbenzoyl-diphenyl-phosphine oxide

DAR1173: 2-hydroxy-2-methyl-1-phenyl-propane-1-one

5. Other Additives

Thickener

D2528: methacrylic acid ester-based polymer (manufactured by Negami Chemical Industrial Co., Ltd.)

R805: silica fine particle (manufactured by NIPPON AEROSIL CO., LTD.)

White Pigment

JR-805: titanium dioxide (manufactured by TAYCA CORPORATION)

Device and Apparatus Used in Examples of the Present Invention

Ultraviolet photopolymerization device: AKZENTZ UV lamp (Model UVL-92, manufactured by TAKIGAWA Co., LTD.)

Instron Universal Testing Machine [manufactured by INSTRON CO.]

Evaluation of Materials of Antibacterial Artificial Nail Composition

Preparation of Antibacterial Artificial Nail Composition

According to each formulation shown in Table 1, materials were weighed and mixed under an atmospheric pressure at 50° C. for 16 hours. Then, the mixture was degassed using an autorotation and revolution type mixer under 40 to 45 Torr to obtain antibacterial artificial nail compositions of the present invention as a uniform high-viscosity transparent liquid.

TABLE 1

Preparation Table of antibacterial artificial nail composition

| Items Examples | Amount (parts by weight) | | | | | | | |
|---|---|---|---|---|---|---|---|---|
| | UDMA | ML-12G | BisMEP | DAR1173 | Antibacterial filler A | Antibacterial filler B | MAPO | D2528 |
| Example 1 | 62.0 | 30.0 | 8.0 | 2.0 | 0.0 | 0.0 | 2.0 | 15.0 |
| Example 2 | 52.0 | 40.0 | 8.0 | 2.0 | 0.0 | 0.0 | 2.0 | 15.0 |
| Example 3 | 42.0 | 50.0 | 8.0 | 2.0 | 0.0 | 0.0 | 2.0 | 15.0 |

Test of Mechanical Strength of Cured Article of Antibacterial Artificial Nail Composition As a test of the mechanical strength of a cured article of an antibacterial artificial nail composition, a test of the bending strength was carried out. The shape and size of a test piece were set in conformity of JIS T6514: 2005 (Test of bending strength of dental filling composite resin). The test piece was produced by filling a mold made of stainless steel in conformity of JIS T6514: 2005 with an antibacterial artificial nail composition, followed by pressure welding using a glass plate. Using an ultraviolet photopolymerization device AKZENTZ UV lamp (Model UVL-92, manufactured by TAKIGAWA CO., LTD.), upper and lower surfaces were irradiated with light for 120 seconds to obtain a cured article of an antibacterial artificial nail composition. Immediately after production of the cured article, a test of the bending strength of the cured article of the antibacterial artificial nail composition cured article was carried out by using Instron Universal Testing Machine. The crosshead speed was set at 10 mm/min and the number of test pieces was 6. In Table 2, the results of a test of the bending strength of the cured article of the antibacterial artificial nail composition (average of 6 test pieces) are shown.

TABLE 2

Results of test of bending strength of antibacterial artificial nail composition

| Antibacterial artificial nail composition | Maximum value of bending strength [MPa] | Bending elastic modulus [MPa] |
|---|---|---|
| Example 1 | 11.9 | 156.1 |
| Example 2 | 5.4 | 51.8 |
| Example 3 | 4.0 | 31.7 |

The bending strength of the antibacterial artificial nail compositions of Example 1, Example 2 and Example 3 shown in Table 2 was a proper value for an artificial nail material.

Measurement of Surface Gloss of Cured Article of Antibacterial Artificial Nail Composition As the evaluation of beautiful appearance of the antibacterial artificial nail composition, surface gloss of the cured article of the antibacterial artificial nail composition was carried out. On a glass plate, the antibacterial artificial nail composition was applied through a spacer in a thickness of 200 μm and then photopolymerized using an ultraviolet photopolymerization device AKZENTZ UV lamp (Model UVL-92, manufactured by TAKIGAWA CO., LTD.). The photopolymerization was conducted by changing the polymerization time under exposure to light. After lapse of a fixed time, a surface unpolymerized layer was wiped off by cotton impregnated with ethanol and surface gloss was measured. Using Gloss Cheker IG331 manufactured by HORIBA, Ltd. as a measuring device, 60° surface gloss was measured. The results are shown in Table 3.

TABLE 3

Results of measurement of surface gloss of cured article of antibacterial artificial nail composition

| Antibacterial artificial nail composition | Irradiation time [second] | | |
|---|---|---|---|
| | 30 | 60 | 120 |
| Example 1 | 87 | 91 | 98 |
| Example 2 | 81 | 89 | 89 |
| Example 3 | 87 | 93 | 93 |

The measured surface gloss of the cured article of the antibacterial artificial nail compositions of Example 1, Example 2 and Example 3 shown in Table 3 was a proper value for an artificial nail material.

Antibacterial Test of Antibacterial Artificial Nail Composition

Preparation of Antibacterial Artificial Nail Composition

According to each formulation described in Table 4 and Table 5, materials were weighed and mixed under an atmospheric pressure at 50° C. for 16 hours. Then, the mixture was degassed using an autorotation and revolution type mixer under 40 to 45 Torr to obtain antibacterial artificial nail compositions of the present invention and compositions of Comparative Examples as a uniform high-viscosity transparent liquid.

TABLE 4

Preparation Table 1 of antibacterial artificial nail composition

| Materials | Amount [parts by weight] | | | | | |
|---|---|---|---|---|---|---|
| | Example 4 | Example 5 | Example 6 | Example 7 | Example 8 | Example 9 |
| UDAO | 32.0 | 32.0 | 32.0 | 30.0 | 30.0 | 30.0 |
| ML-12G | 24.0 | 0.0 | 0.0 | 0.0 | 0.0 | 0.0 |
| ML-8G | 0.0 | 24.0 | 0.0 | 0.0 | 0.0 | 0.0 |
| ML | 0.0 | 0.0 | 24.0 | 0.0 | 0.0 | 0.0 |
| Antibacterial filler A | 0.0 | 0.0 | 0.0 | 0.5 | 7.5 | 0.0 |
| Antibacterial filler B | 0.0 | 0.0 | 0.0 | 0.0 | 0.0 | 0.5 |
| 14EG | 0.0 | 0.0 | 0.0 | 30.0 | 30.0 | 0.0 |
| 2HEMA | 0.0 | 0.0 | 0.0 | 0.0 | 0.0 | 30.0 |
| UDMA | 40.0 | 40.0 | 40.0 | 36.0 | 36.0 | 36.0 |
| BisMEP | 4.0 | 4.0 | 4.0 | 4.0 | 4.0 | 4.0 |
| MAPO | 1.0 | 1.0 | 1.0 | 1.0 | 1.0 | 1.0 |
| DAR1173 | 1.0 | 1.0 | 1.0 | 1.0 | 1.0 | 1.0 |
| R805 | 2.0 | 2.0 | 2.0 | 2.0 | 2.0 | 2.0 |

TABLE 5

Preparation Table 2 of antibacterial artificial nail composition

| | Amount [parts by weight] | | | | | |
|---|---|---|---|---|---|---|
| Materials | Example 10 | Example 11 | Example 12 | Comparative Example 1 | Comparative Example 2 | Comparative Example 3 |
| UDAO | 30.0 | 32.0 | 32.0 | 30.0 | 30.0 | 30.0 |
| ML-12G | 0.0 | 0.0 | 24.0 | 0.0 | 0.0 | 0.0 |
| ML-8G | 0.0 | 0.0 | 0.0 | 0.0 | 0.0 | 0.0 |
| ML | 0.0 | 0.0 | 0.0 | 0.0 | 0.0 | 0.0 |
| Antibacterial filler A | 7.5 | 0.5 | 0.5 | 0.0 | 0.0 | 0.0 |
| Antibacterial filler B | 0.0 | 0.5 | 0.5 | 0.0 | 0.0 | 0.0 |
| 14EG | 30.0 | 0.0 | 0.0 | 0.0 | 30.0 | 0.0 |
| 2HEMA | 0.0 | 0.0 | 0.0 | 0.0 | 0.0 | 30.0 |
| UDMA | 36.0 | 40.0 | 40.0 | 36.0 | 36.0 | 36.0 |
| BisMEP | 4.0 | 4.0 | 4.0 | 4.0 | 4.0 | 4.0 |
| MAPO | 1.0 | 1.0 | 1.0 | 1.0 | 1.0 | 1.0 |
| DAR1173 | 1.0 | 1.0 | 1.0 | 1.0 | 1.0 | 1.0 |
| R805 | 2.0 | 2.0 | 2.0 | 2.0 | 2.0 | 2.0 |

In conformity of ISO14356, a test of antibacterial properties of the artificial nail composition was carried out. Device and apparatus used (1) Materials Petri dish: each measuring about 60 mm in inner diameter and 15 mm in depth (one is for a test sample, and the other one is for a control test sample).

(2) Kinds of Culture

*Rhizopus nigricans, Aspergillus nidulans* and *Penicilium glaucum.*

(3) Relative Humidity Chamber

Temperature: 23±2° C., Humidity: 95±5%.

Preparation of Antibacterial Test

An agar culture medium is spread over a petri dish and one kind of a culture is inoculated. A cured test piece (shape: f20) is placed on a culture medium, and a sample is absent in case of a control. Both petri dish samples are capped and allowed to stand in a relative humidity chamber for 7 days.

Judgment of Results of Antibacterial Properties

The degree of growth of culture is judged.

Evaluation 0: No growth of culture is observed.

Evaluation 1: Slight growth of culture is observed.

Evaluation 2: Little growth of culture is observed.

Evaluation 3: Intermediate growth of culture is observed.

Evaluation 4: Considerable growth of culture is observed.

Results of Antibacterial Test

TABLE 6

Test results 1 of antibacterial properties

| Items | Example 4 | Example 5 | Example 6 | Example 7 | Example 8 | Example 9 |
|---|---|---|---|---|---|---|
| Evaluation of antibacterial properties Score | 0 | 0 | 0 | 0 | 0 | 0 |

TABLE 7

Test results 2 of antibacterial properties

| Items | Example 10 | Example 11 | Comparative Example 1 | Comparative Example 2 | Comparative Example 3 |
|---|---|---|---|---|---|
| Evaluation of antibacterial properties Score | 0 | 0 | 3 | 3 | 3 |

Note:
Cultures are *Rhizopus nigricans, Aspergillus nidulans,* and *Penicilium glaucum,* and score was the same with respect to all cultures.

As is apparent from the results shown in Table 6 and Table, the antibacterial artificial nail composition of the present invention has antibacterial properties.

What is claimed is:

1. A method of forming a cured article having an antibacterial effect, comprising applying an antibacterial artificial nail composition on a surface of a natural nail or an artificial nail, and polymerizing the composition, wherein the antibacterial artificial nail composition comprises:

bis[2-(methacryloxy)ethyl]phosphate; and urethane acrylate oligomer having two acrylic groups and a molecular weight of 15,000 Da; and a polymerization initiator; and a component selected from the group consisting of (A) a compound having at least one radical polymerizable unsaturated double bond and an antibacterial group in the molecule, (B) an antibacterial filler, and combinations thereof.

2. The method according to claim 1, wherein the compound (A) having at least one radical polymerizable unsaturated double bond and an antibacterial group in the molecule is a (meth)acrylic acid ester compound having a 10-undecenoxy group and an ethoxy group (compound A) represented by the following general formula I:

General formula 1

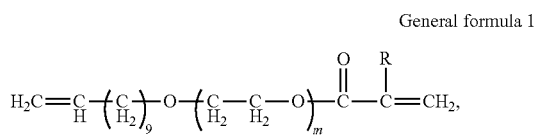

wherein m represents an integer of 0 to 18, and R represents a hydrogen atom or a methyl group.

3. The method according to claim 1, wherein the antibacterial filler (B) is a cation-substituted type hydroxyapatite-based antibacterial filler represented by the general formula 2 and/or a zeolite-based antibacterial filler represented by the general formula 3:

$$Ca_{10-q}M_{2q/n}(PO_4)_6(OH)_2 \qquad \text{General formula 2}$$

$$XM_{2/n}O \cdot Al_2O_3 \cdot YSiO_2 \cdot ZH_2O \qquad \text{General formula 3,}$$

wherein, in the general formula 2, M represents one or more kinds of metallic elements selected from Ag, Cu, Ni, Zn and Pd, n represents a valency of a metallic element M, and q represents a positive number satisfying a relation: $q \leq 0.0502 \, n/m$ with an atomic weight m and a valency n of the metallic element M and, in the general formula 3, M represents a mono- or divalent metal ion, n represents a valency of metal, and X, Y and Z each represents an oxide coefficient, a silica coefficient or the number of water of crystallization.

4. The method according to claim 1, wherein the composition contains the compound (A) having at least one radical polymerizable unsaturated double bond and an antibacterial group in the molecule represented by the general formula 1 in an amount of 0.1 to 70% by weight based on the entire amount of the composition.

5. The method according to claim 2, wherein the composition contains the compound (A) having at least one radical polymerizable unsaturated double bond and an antibacterial group in the molecule represented by the general formula 1 in an amount of 0.1 to 70% by weight based on the entire amount of the composition.

6. The method according to claim 3, wherein the composition contains the compound (A) having at least one radical polymerizable unsaturated double bond and an antibacterial group in the molecule represented by the general formula 1 in an amount of 0.1 to 70% by weight based on the entire amount of the composition.

7. The method according to claim 2,
wherein the antibacterial filler (B) is a cation-substituted type hydroxyapatite-based antibacterial filler represented by the general formula 2:

$$Ca_{10-q}M_{2q/n}(PO_4)_6(OH)_2 \qquad \text{General formula 2,}$$

wherein, in the general formula 2, M represents one or more kinds of metallic elements selected from Ag, Cu, Ni, Zn and Pd, n represents a valency of a metallic element M, and q represents a positive number satisfying a relation: $q \leq 0.0502 \, n/m$ with an atomic weight m and a valency n of the metallic element M, and wherein the composition contains the cation-substituted type hydroxyapatite-based antibacterial filler represented by the general formula 2 in an amount of 0.5% to 7.5% by weight based on the entire amount of the composition.

8. The method according to claim 3, wherein the composition contains the cation-substituted type hydroxyapatite-based antibacterial filler represented by the general formula 2 in an amount of 0.5% to 7.5% by weight based on the entire amount of the composition.

9. The method according to claim 6, wherein the composition contains the cation-substituted type hydroxyapatite-based antibacterial filler represented by the general formula 2 in an amount of 0.5% to 7.5% by weight based on the entire amount of the composition.

10. The method according to claim 2,
wherein the antibacterial filler (B) is a zeolite-based antibacterial filler represented by the general formula 3:

$$XM_{2/n}O \cdot Al_2O_3 \cdot YSiO_2 \cdot ZH_2O \qquad \text{General formula 3,}$$

wherein, in the general formula 3, M represents a mono- or divalent metal ion, n represents a valency of metal, and X, Y and Z each represents an oxide coefficient, a silica coefficient or the number of water of crystallization, and wherein the composition contains the zeolite-based antibacterial filler represented by the general formula 3 in an amount of 0.5% to 7.5% by weight based on the entire amount of the composition.

11. The method according to claim 3, wherein the composition contains the zeolite-based antibacterial filler represented by the general formula 3 in an amount of 0.5% to 7.5% by weight based on the entire amount of the composition.

12. The method according to claim 6, wherein the composition contains the zeolite-based antibacterial filler represented by the general formula 3 in an amount of 0.5% to 7.5% by weight based on the entire amount of the composition.

13. The method according to claim 8, wherein the composition contains the zeolite-based antibacterial filler represented by the general formula 3 in an amount of 0.5% to 7.5% by weight based on the entire amount of the composition.

* * * * *